US00PP17381P3

(12) United States Plant Patent
Khanizadeh

(10) Patent No.: US PP17,381 P3
(45) Date of Patent: Jan. 23, 2007

(54) STRAWBERRY PLANT AND FRUIT NAMED 'LA CLE DES CHAMPS'

(50) Latin Name: *Fragaria×ananassa*
Varietal Denomination: La Cle des Champs

(75) Inventor: Shahrokh Khanizadeh, Baie d'Urfe (CA)

(73) Assignee: Agriculture & Agri-Food Canada (CA)

( * ) Notice: Subject to any disclaimer, the term of this patent is extended or adjusted under 35 U.S.C. 154(b) by 0 days.

(21) Appl. No.: 10/897,717

(22) Filed: Jul. 23, 2004

(65) Prior Publication Data

US 2005/0155122 P1 Jul. 14, 2005

(30) Foreign Application Priority Data

Jul. 23, 2003 (CA) ..... 03-3781

(51) Int. Cl.
*A01H 5/00* (2006.01)

(52) U.S. Cl. ..... Plt./208

(58) Field of Classification Search ..... Plt./208
See application file for complete search history.

(56) References Cited

U.S. PATENT DOCUMENTS

PP11,446 P * 7/2000 Jelenkovic et al. ..... Plt./208

OTHER PUBLICATIONS

UPOV ROM GTITM Computer Database, GTI Jouve Retrieval Software 2005/03 Citation for 'La Cle des Champs'.*

* cited by examiner

*Primary Examiner*—Wendy Haas
(74) *Attorney, Agent, or Firm*—Cantor Colburn LLP

(57) ABSTRACT

The present invention relates to a new and distinct variety of strawberry named "La Cle des Champs". The variety is botanically identified as *Fragaria×ananassa*. The new variety is distinguished from other varieties by a number of properties including but not limited to: shape and lengthy leaves; fruit color and texture; and disease and temperature hardiness.

9 Drawing Sheets

Latin name of the genus and species of the plant claimed: The variety is botanically identified as *Fragaria×ananassa*.
Variety denomination: La Cle des Champs.

BACKGROUND OF THE INVENTION

The new variety 'La Cle des Champs' originated from the controlled cross of the strawberry plants "SJ89244-6E" and "SJ8518-11" made in 1993. Evaluations have been ongoing since 1994. Selection criteria include winter hardiness, fruit quality, shelf life and disease resistance. 'La Cle des Champs' were planted in 2002 at l'Acadie, Québec. The plots were grown in matted rows approximately 2.5 m in length, and consisted of four replicates per variety. Evaluations were made on plants during 2002–2003 growing seasons.

SUMMARY OF THE INVENTION

The present invention relates to a new and distinct variety of strawberry named 'La Cle des Champs'. The variety is botanically identified as *Fragaria×ananassa*. The new variety is distinguished from other varieties by a number of characteristics as set forth below.

COMPARISON TO SIMILAR VARIETIES

The low temperature tolerance of 'La Cle des Champs' is high whereas in 'Jewel,' U.S. Plant Pat. No. 5,897 (hereinafter 'Jewel') it is medium. The terminal leaflets of 'La Cle des Champs' are longer than they are broad whereas they are as long as they are broad in 'Jewel.' The leaves of 'La Cle des Champs' have weak interveinal blistering whereas it is very weak in 'Jewel.' 'Le Cle des Champs' is resistant to powdery mildew (*Sphaerotheca macularis* Wallr. Ex Fr.) and leaf scorch (*Diplocarpon earlina* Ell. & Ev.), whereas Jewel is moderately resistant. 'La Cle des Champs' is moderately susceptible to susceptible to *Verticillium* wilt whereas 'Jewel' is moderately susceptible. 'La Cle des Champs' is moderately susceptible to susceptible to leaf spots (*Mycosphaerella fragariae* Tul. Lindau) whereas 'Jewel' is moderately resistant to moderately susceptible.

BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
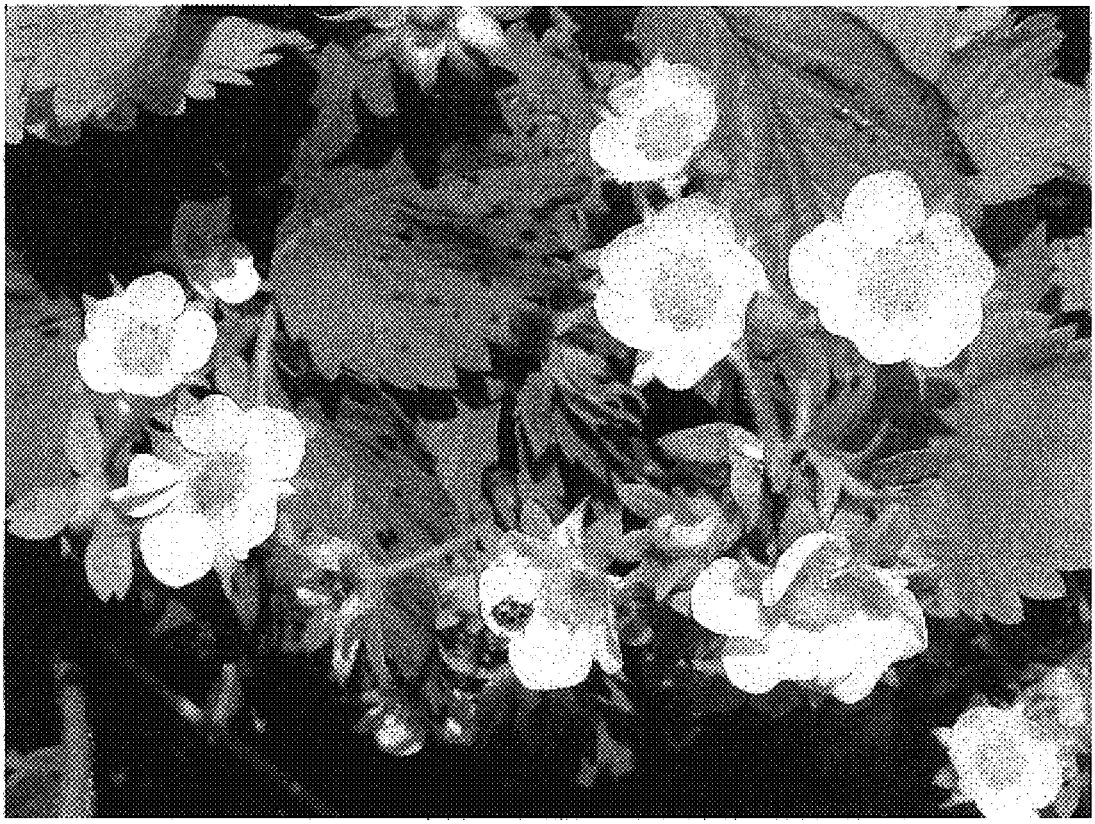
FIG. 1 illustrates the upper side of the flowers and the plant.
Figure 2:
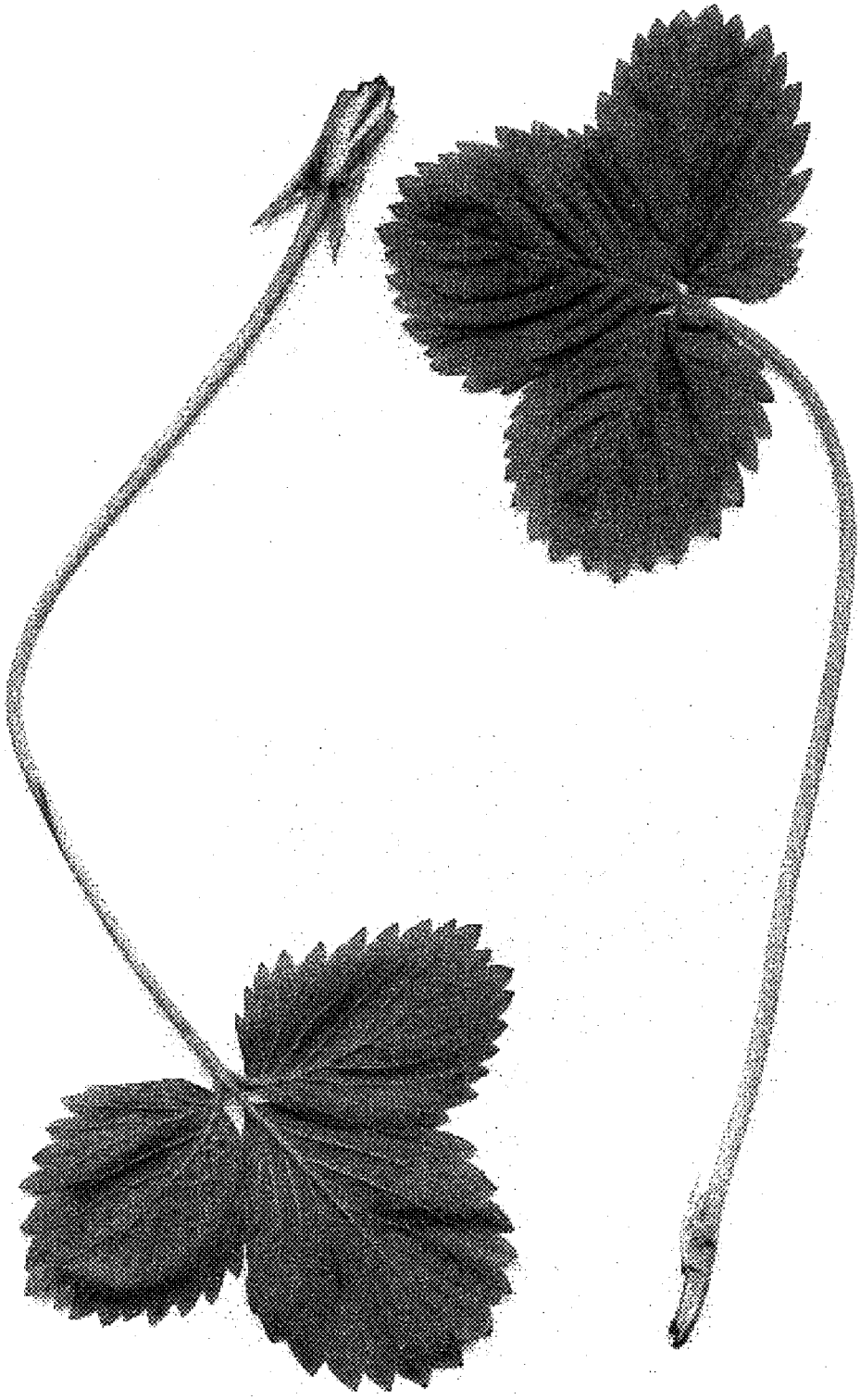
FIG. 2 illustrates the leaves of the plant.
Figure 3:
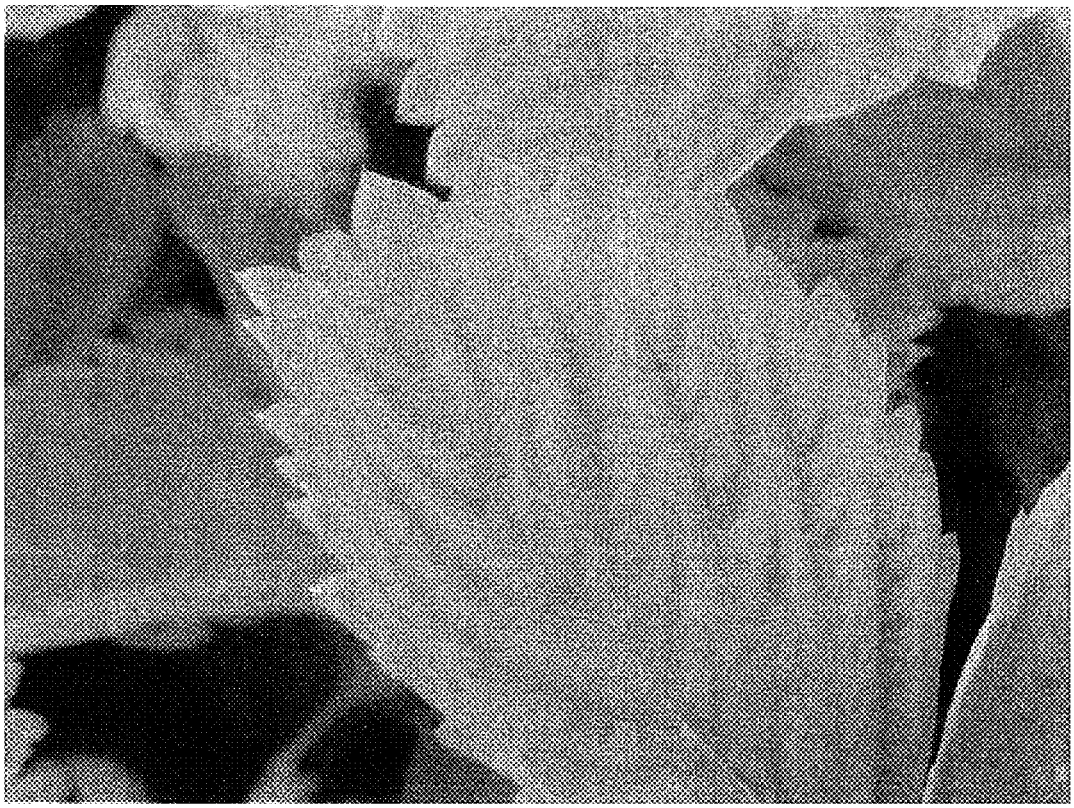
FIG. 3 illustrates the leaves of the plant.
Figure 4:
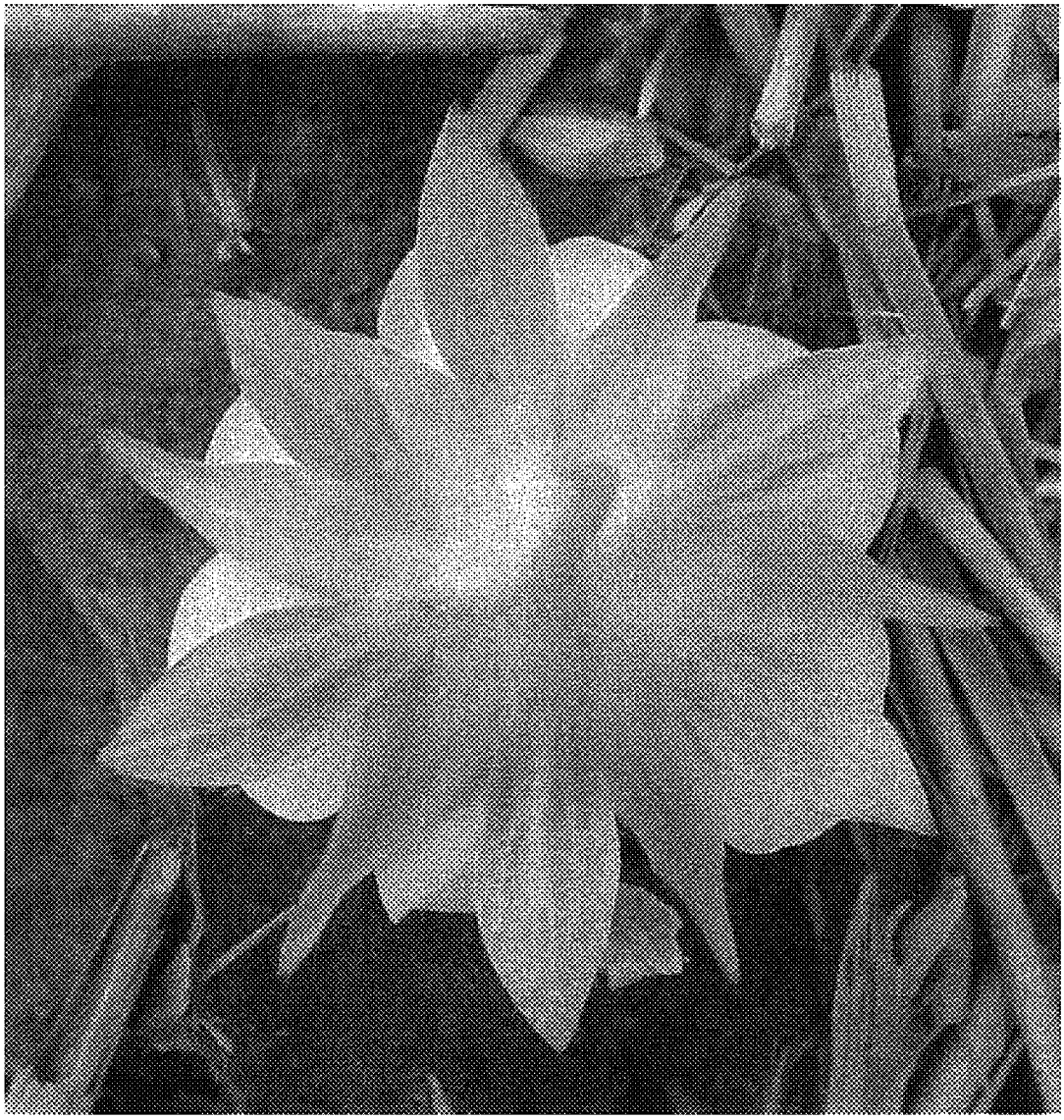
FIG. 4 illustrates the under side of the flowers.
Figure 5:
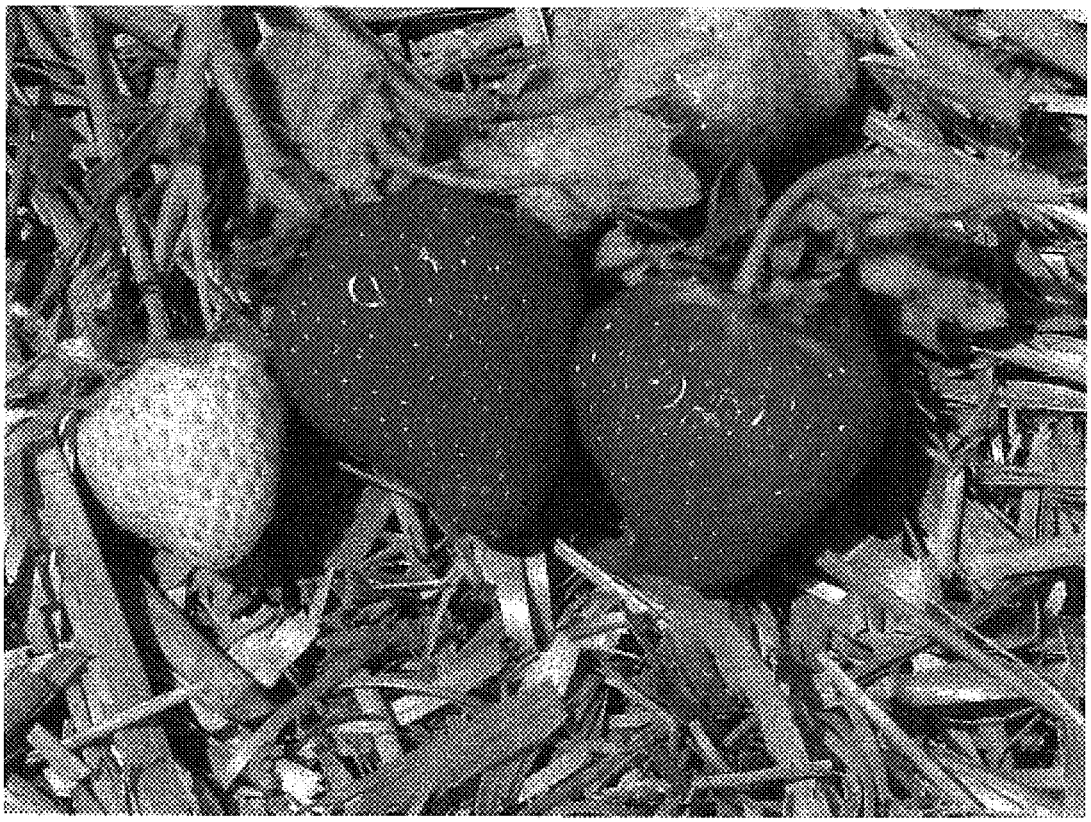
FIG. 5 illustrates a close-up of the fruit.
Figure 6:
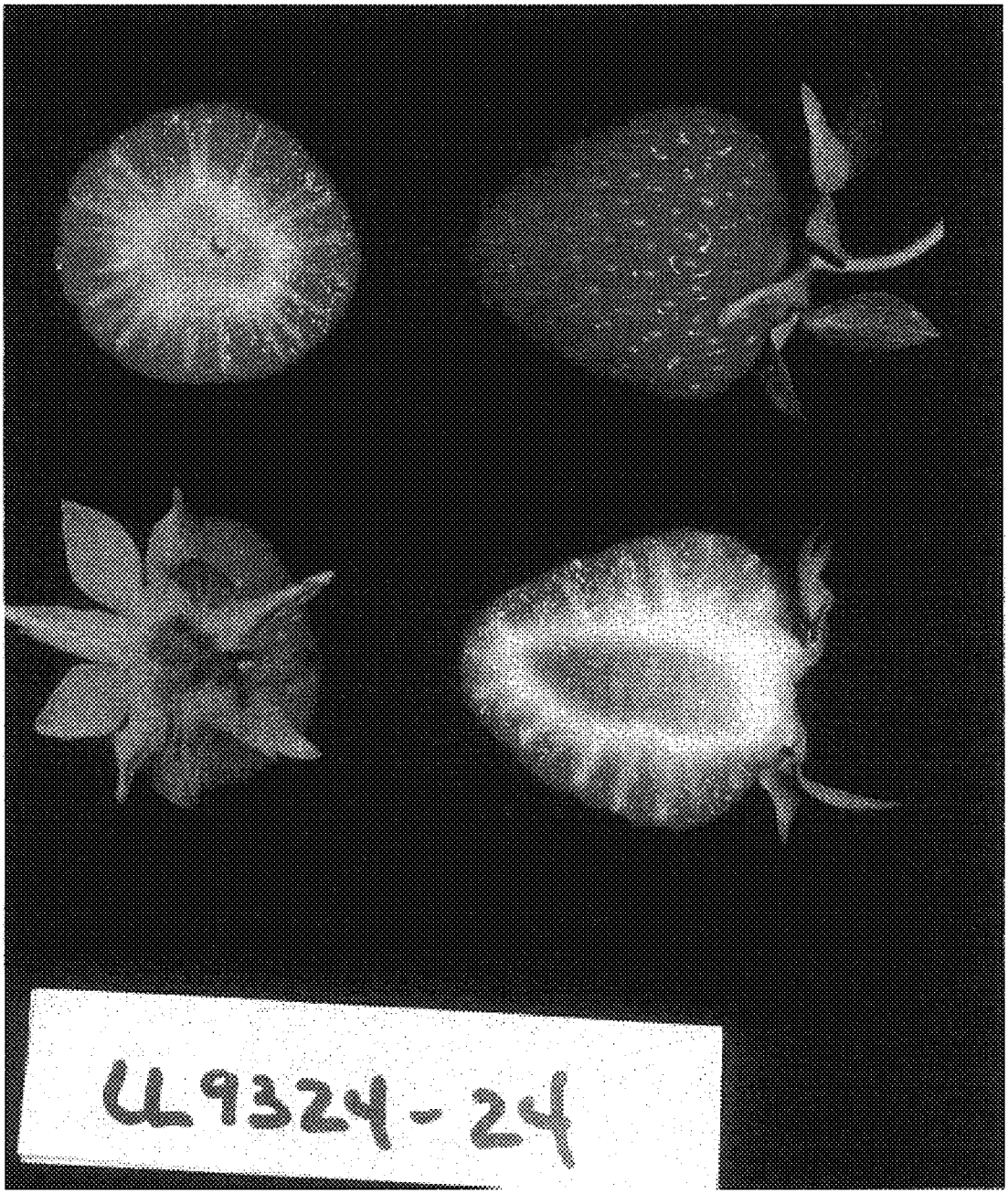
FIG. 6 illustrates the fruit in longitudinal and transversal cross-sections and upper side and side of the fruit.
Figure 7:
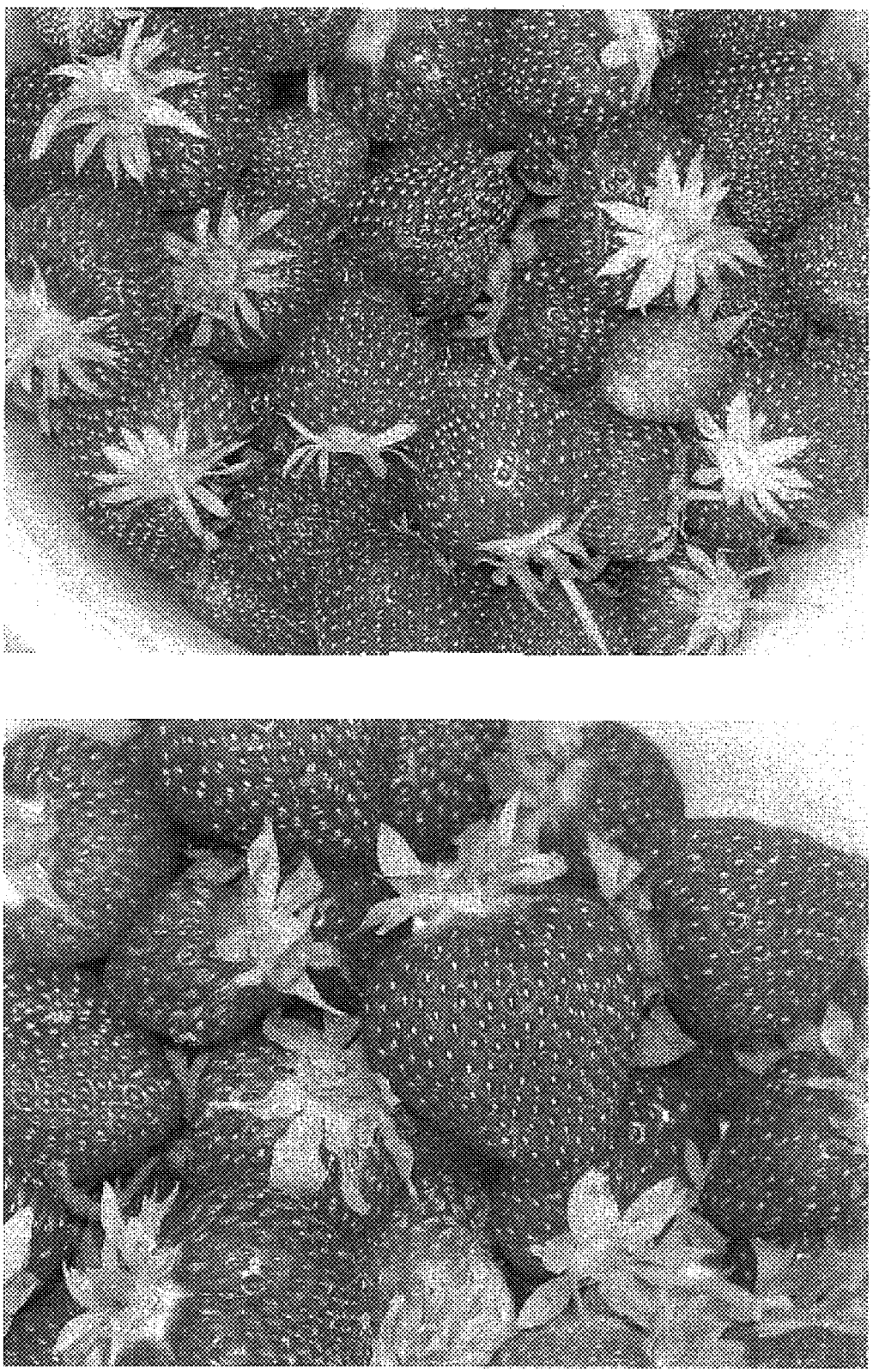
FIG. 7 illustrates a close-up of the fruit compared to 'Jewel.'
Figure 8:
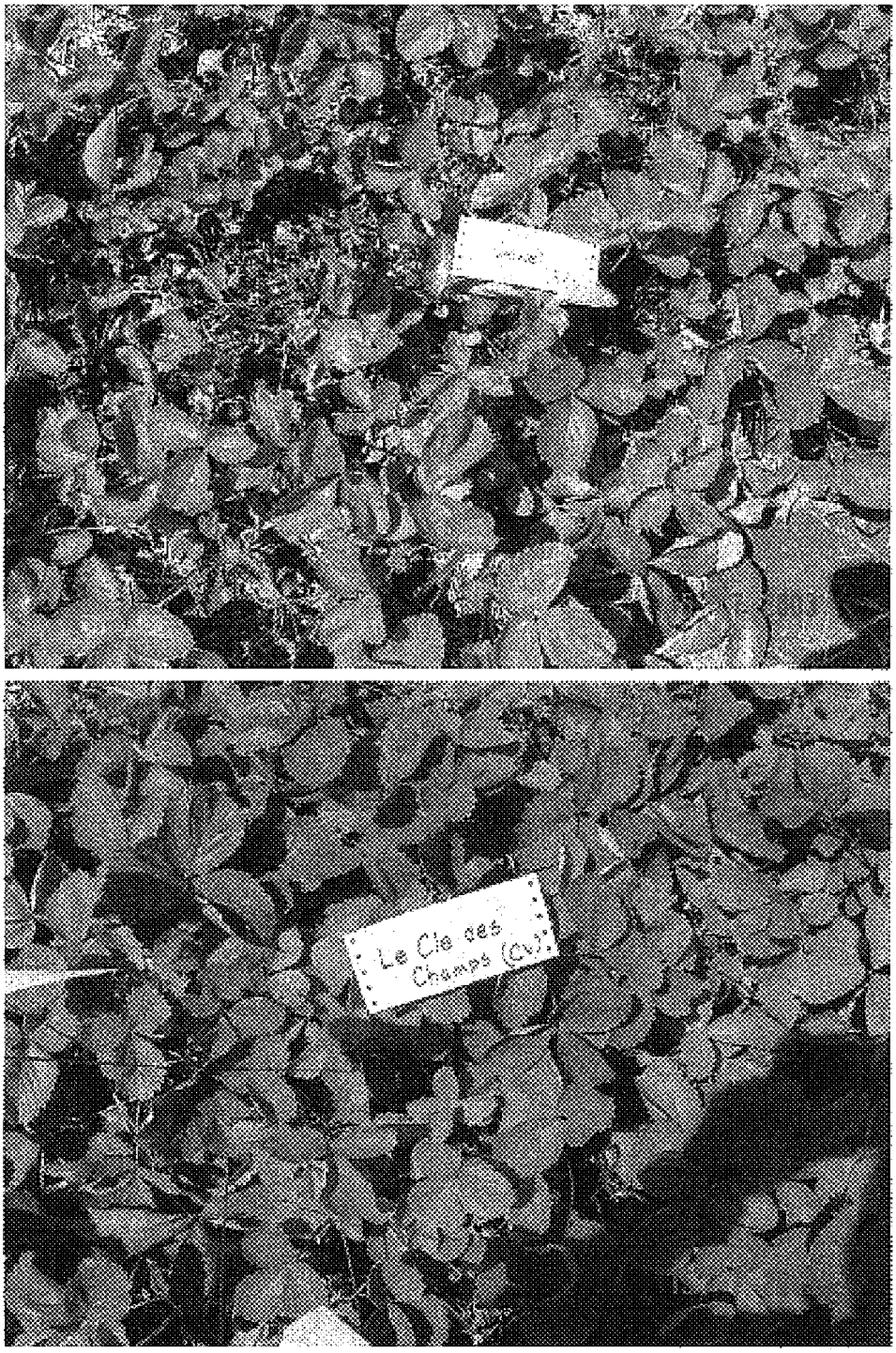
FIG. 8 illustrates the leaves of the plant compared to 'Jewel.'
Figure 9:
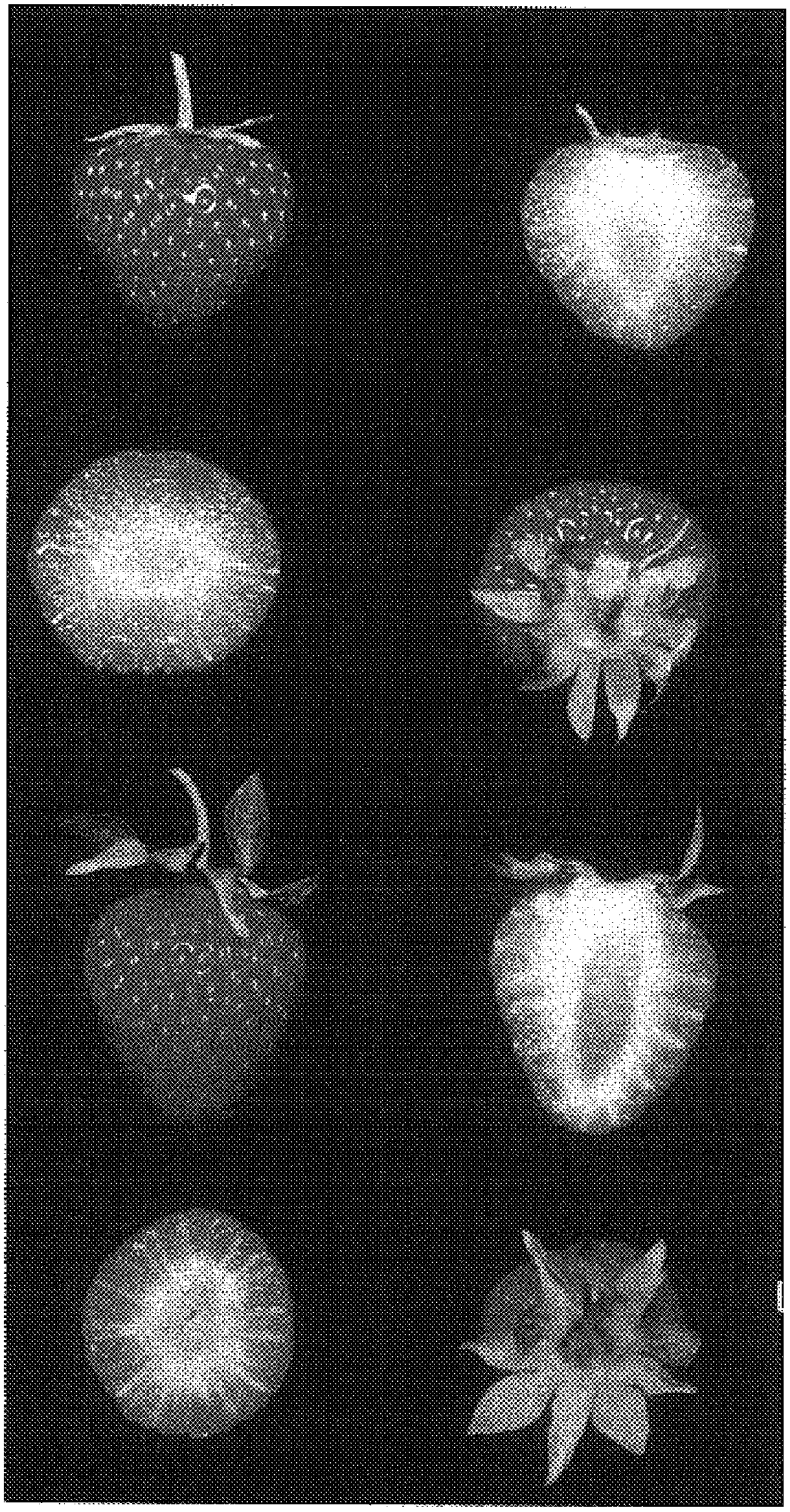
FIG. 9 illustrates the fruit in longitudinal and transversal cross-sections and upper side and side of the fruit compared to 'Jewel.'

The following detailed description of the new variety is based upon observations taken of plants and fruit grown in l'Acadie, Québec. Observations of 'La Cle des Champs' and 'Jewel' were taken in side by side comparison in 2002–2003 growing season. This description is in accordance with UPOV terminology. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

PROPAGATION

The new variety is principally propagated by way of solons. Although propagation by solons is presently preferred, other known methods of propagating strawberry plants may be employed. 'Le Cle Des Champs' resulted from crossing the selections 'SJ89244-6E' and 'SJ8518-11' at AAFC in Quebec. Both parent plants are unpatented, non-commercial varieties kept at an AAFC gene bank. 'SJ89244-6F' is not a true June bearing variety and produces flowers 2–3 times during the summer, contrary to the 'Le Cle Des Champs,' which flower only once during the growing season.

CHARACTERISTICS OF THE NEW VARIETY

'La Cle des Champs' is a June-bearing strawberry variety with mid-season flowering and maturity. Plants are globose in habit, with strong vigour and high tolerance to low temperatures. The leaves are medium green with a slightly convex profile and weak blistering. There are three leaflets present. The terminal leaflet has a cupped profile and is slightly longer than broad. The terminal leaflet has an obtuse shaped base and the margin teeth are acute to obtuse in shape. The petiole has medium to dense pubescence with the hairs positioned outwards. 'Le Cle des Champs' produces many stolons which are medium to thick.

The medium to large flowers are positioned beneath to level with the foliage. The calyx is the same size to larger in diameter than the corolla and the inner calyx is smaller than to the same size as the outer calyx. The flower petals are touching to overlapping. The petal length/width ratio is broader than long.

The fruiting truss is semi-erect to prostrate and long. The fruit is longer than broad and ranges in size from medium to very large. The fruit is conical in shape with slight to moderate differences between the shape of the primary and secondary fruits. The achene band is medium to broad and the fruit surface is even. 'La Cle des Champs' has slightly uneven orange-red to red skin colour with strong glossiness. The achenes are inserted level with to above the fruit surface. The calyx is set above the fruit and the calyx segments are reflexed. The calyx is the same size as to larger than the fruit in diameter and adheres strongly to the fruit. The fruit flesh is firm to extremely firm with an uneven, orange red colour. The fruit has medium sweetness, acidity and texture. 'La Cle des Champs' is resistant to powdery mildew and leaf scorch. It is resistant to *Verticillium* wilt and leaf spots and moderately susceptible to all races of Red stele.

The plants and control were two year old plants that were cultivated and maintained as those grown commercially. 'Cle Des Champs' is tested in L'Acadie Quebec and also in several other areas of Eastern-Central Canada. The data presented here is from L'Acadie Experimental Farm of AAFC, where the winter temperature goes down to −30 degrees C., with warm and humid summers (drought some seasons, constant rain in others). These conditions make 'Le Cle Des Champs' a good, stress-resistant variety.

The dates of first and full bloom in the location of culture is 10% bloom as of June 3, with full bloom as June 7. The dates of first and last pick in the location of culture were June 24 (1st picking date) and July 9 (last picking date). The typical and observed plant height and diameter was a typical height of 22 cm–26 cm and observed height of 18 cm, with a typical diameter of 16 cm and an observed diameter of 16 cm. More information regarding vigor, such as growth over a specified period of time is not available.

The specific high and low temperature tolerance of the claimed plant was a high of 35 C., and a low that was observed at −31 C. at the L'acadie experimental farm (with 10 cm of straw cover).

RIIS color designations for the upper and lower leaf surfaces are RIIS137C for the upper and RHS138C for the lower. Petiole length, diameter and color with reference to the RIIS color chart included a length of 15.9 cm, a diameter 3.1 mm, and a color of RHS144B (before bloom). Leaf length and width in centimeters or inches were 7.9 cm and 6.8 cm respectively. Upper and lower leaf surface texture was fairly smooth (interveinal blistering was weak). Leaf apex shape was rounded. Stolon length, diameter and color with reference to the employed color chart included a length of 91–120 cm, a diameter of 2.1 mm, and a color of faded RIIS 181A over the entire surface. Flower color with reference to the employed color chart was pure white.

Flower diameter and depth were 2.7–3.4 cm and 2 mm respectively. Petal shape was flat globose, with a length of 1.0–1.4 cm and a width of 1.1–1.6 cm, and a fairly flat apex and base. Petal number was 5.

Calyx color was RHS 138A, calyx diameter was 3.1–4.0 cm, and sepal number was 11. Sepal length was 1.3–1.6 cm and sepal width was 0.2 cm, while sepal overall shape was lanceolate or deltoid, including an acute apex, broad base, and continuous margin. Pedicel length and diameter are not available. Pedicel color with reference to the employed color chart was RHS138A.

Length and width of primary and secondary fruit included a primary length and width of 3.9 cm and 3.4 cm respectively, and a secondary length and width of 3.4 cm and 2.9 cm respectively. Color with respect to the employed color chart for the fruit skin and fruit flesh was RHS44A & RHS 46A (skin) RHS44A (flesh) respectively. Achene color was RHS150C. The fruit has a % brix of 7.7 to 9.4.

TABLE 1

Total yield, fruit weight and ripening season of 'Clé des Champs' and comparison genotypes at the L'Acadie site.

| Genotype | Total yield[z] ($g.m^{-1}$) | Wt./fruit[z] (g) | Ripening season[y] | Hardiness |
|---|---|---|---|---|
| Kent | 2821.5 a | 10.42 b | EM | Very hardy |
| Clé des Champs | 1633.3 ab | 12.88 a | M | Very hardy |
| Jewel | 1390.8 b | 10.85 ab | M | Less hardy |
| LSD | 1213.7 | 2.42 | | |

[z]Averaged over 4 replicates from two field second year plantings (2003–2004), data taken from a 1 meter long representative portion of a 2 meter matted row (width 50 cm).
[y]EM = Early midseason, M = midseason,

TABLE 3

Groups of phenolic compounds (ppm) and antioxidant property of Jewel vs Clédes Champs grown at L' Acadie site in 2003.

| Genotype | Antho-cyanins | Hydroxy-cinnamic acids | Flav-onols | Ellagic acids | Benzoic acids | Total |
|---|---|---|---|---|---|---|
| Clédes Champs | 114.46 b | 5.88 fg | 4.48 f | 2.63 fg | 27.19 d | 154.64 b |
| Jewel | 140.21 a | 4.34 gh | 6.40[e] | 2.62 fg | 15.60 g | 169.17 a |
| $LSD_{0.05}$ | 6.51 | 1.68 | 0.89 | 0.36 | 1.55 | 6.68 |

Groups of phenolic compounds were quantified as follows: ellagic acids as ellagic acid, benzoic acids as gallic acid, hydroxycinnamic acids as p-coumaric acid, flavonols as quercetin-3-galactoside, and anthocyanins as cyanidin-3-galactoside. Values followed by the same letter are not significantly different.

What is claimed is:

1. A new and distinct variety of strawberry plant, substantially as shown and described.

* * * * *